US005770607A

United States Patent [19]
Honbo et al.

[11] Patent Number: 5,770,607
[45] Date of Patent: Jun. 23, 1998

[54] AQUEOUS LIQUID COMPOSITION FOR EXTERNAL USE

[75] Inventors: Toshiyasu Honbo, Kobe; Sachiyo Tanimoto, Kadoma, both of Japan; Hiromitsu Yoshida, Leiden, Netherlands; Takehisa Hata, Nagaokakyo, Japan; Sotoo Asakura, Kyoto, Japan; Yasuto Koyama, Itami, Japan; Youhei Kiyota, Ikeda, Japan

[73] Assignee: Fujisawa Pharmaceutical Co., Ltd., Osaka, Japan

[21] Appl. No.: 276,495

[22] Filed: Jul. 18, 1994

Related U.S. Application Data

[63] Continuation of Ser. No. 853,020, Mar. 18, 1992, abandoned, which is a continuation of Ser. No. 546,883, Jul. 2, 1990, abandoned.

[30] Foreign Application Priority Data

Jul. 5, 1989 [JP] Japan .................................... 1-176637

[51] Int. Cl.$^6$ .......................... A61K 31/44; A61K 31/515
[52] U.S. Cl. ........................ 514/302; 514/271; 514/279; 514/299; 514/912
[58] Field of Search ................................... 514/271, 279, 514/299, 302, 912

[56] References Cited

FOREIGN PATENT DOCUMENTS

| 315978 | 8/1988 | European Pat. Off. . |
| 356399 | 7/1990 | European Pat. Off. . |
| 240773 | 8/1991 | European Pat. Off. . |

OTHER PUBLICATIONS

European Search Report against EP 90 11 2655 dated Sep. 5, 1991.
Ocular Pharmacology, Fourth Edition, 1978, p. 507.
Physicions' Desk Reference for Ophthamology, 16 Edition, 1988. p. 126.
Chemical Abst. 108:44058c (1988). Ueda et al.

*Primary Examiner*—Zohreh Fay
*Attorney, Agent, or Firm*—Oblon, Spivak, McClelland, Maier & Neustadt, P.C.

[57] ABSTRACT

This invention relates to an aqueous liquid composition for external use which contains a tricyclo compound of the chemical formula (I) presented here-under or a pharmaceutically acceptable salt thereof. More particularly, the invention relates to an aqueous liquid composition for external use characterized in that it contains said tricyclo compound and a water-soluble solubilizer. The composition of the invention is used in medical treatment.

5 Claims, No Drawings

AQUEOUS LIQUID COMPOSITION FOR EXTERNAL USE

This application is a Continuation of application Ser. No. 07/853,020, filed on Mar. 18, 1992, now abandoned, which is a Continuation of application Ser. No. 07/546,883, filed on Jul. 2, 1990, now abandoned.

This invention relates to an aqueous liquid composition for external use which contains a tricyclo compound of the chemical formula (I) presented here-under or a pharmaceutically acceptable salt thereof. More particularly, the invention relates to an aqueous liquid composition for external use characterized in that it contains said tricyclo compound and a water-soluble solubilizer. The composition of the invention is used in medical treatment.

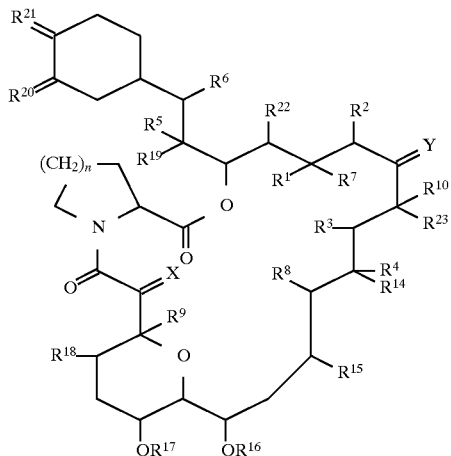

wherein each vicinal pair of substituents [$R^1$ and $R^2$], [$R^3$ and $R^4$], [$R^5$ and $R^6$] independently a) represent two vicinal hydrogen atoms, or
b) form a second bond between the vicinal carbon atoms to which they are attached;

in addition to its significance above, $R^2$ may represent an alkyl group;

$R^7$ represents H, OH, protected hydroxy or O-alkyl, or in conjunction with $R^1$ it may represent =O;

$R^8$ and $R^9$ independently represent H or OH;

$R^{10}$ represents H, alkyl, alkyl substituted by one or more hydroxyl groups, alkenyl, alkenyl substituted by one or more hydroxyl groups, or alkyl substituted by =O;

X represents O, (H,OH), (H,H) or —CH$_2$O—;

Y represents O, (H,OH), (H,H), N—NR$^{11}$R$^{12}$ or N—OR$^{13}$;

$R^{11}$ and $R^{12}$ independently represent H, alkyl, aryl or tosyl;

$R^{13}$, $R^{14}$, $R^{15}$, $R^{16}$, $R^{17}$, $R^{18}$, $R^{19}$, $R^{22}$ and $R^{23}$ independently represent H or alkyl;

$R^{20}$ and $R^{21}$ independently represent O, or they may independently represent ($R^{20}$a,H) and ($R^{21}$a,H) respectively; $R^{20}$a and $R^{21}$a independently represent OH, O-alkyl or OCH$_2$OCH$_2$CH$_2$OCH$_3$ or $R^{21}$a is protected hydroxy;

in addition, $R^{20}$a and $R^{21}$a may together represent an oxygen atom in an epoxide ring;

N is 1, 2 or 3;

in addition to their significances above, Y, $R^{10}$ and $R^{23}$, together with the carbon atoms to which they are attached, may represent a 5- or 6-membered N-, S- or O- containing heterocyclic ring, which may be saturated or unsaturated, and which may be substituted by one or more groups selected from alkyl, hydroxy, alkyl substituted by one or more hydroxyl groups, O-alkyl, benzyl and —CH$_2$Se(C$_6$H$_5$).

The tricyclo compound (I) and pharmaceutically acceptable salt to be employed in this invention have remarkable immunosuppressive, antimicrobial and other pharmacologic activities and are known to be of value in the treatment and prevention of resistance to organ or tissue plantation, graft-versus-host diseases, various autoimmune diseases and infectious diseases (Japanese Kokai Patent Publication NO. 61-148181/1986 and European Patent Publication No. 0323042).

Particularly, FK506, the structural formula of which is presented hereunder, which is produced by fermentation of the FK506-producing microorganisms of the genus Streptomyces, particularly *Streptomyces tsukubaensis* No. 9993 (FERM-BP 927), has been demonstrated to have outstanding immunosuppressive activity and, as such, be of value in the treatment and prevention of diseases in the field of ophthalmology as well.

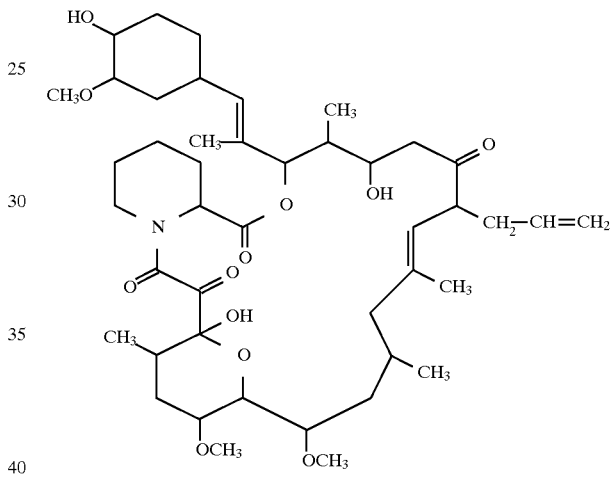

[Chemical name: 17-Allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone]

In using this tricyclo compound (I) of the invention clinically in ophthalmological cases, administration by the oral, intramuscular, intravenous or other systemic route may induce systemic side effects. Therefore, in the field of ophthalmology, eye-drops for topical application which would assure the expected efficacy at a smaller dose and reduce side effects are desirable.

However, while it is well soluble in organic solvents and oily vehicles, the tricyclo compound (I) of the invention is only very sparingly soluble in water. Therefore, in order that the compound (I) may be used in the ophthalmological field, there has been no alternative but to formulate (I) into an oily ophthalmic solution or an eye ointment as it is true with other insoluble drug substances in general.

However, not to speak of the very poor intraocular penetration of the tricyclo compound (I), such an oily ophthalmic solution or an eye ointment tends to induce transient impairment of vision and discomfort. Therefore, these preparations are not as useful as desired for clinical application.

In connection with the ophthalmological application of tricyclo compound (I), the advent of an ophthalmic preparation with improved intraocular transfer kinetics and free of the above-mentioned disadvantages has been keenly demanded.

The inventors of this invention strenuously explored into the relevant technology and found that an aqueous liquid composition obtainable by adding a water-soluble solubilizer to tricyclo compound (I) insures an effective transfer of (I), even at a low dose level, into the body and particularly into the eye, does not cause the above-mentioned visual impairment and discomfort and is not so low in intraocular transfer as ordinary aqueous eye-drops which are rapidly flushed away together with the tears. This invention has been conceived and developed on the basis of the above findings.

This invention is directed to an aqueous liquid composition for external use which is characterized by containing a tricyclo compound (I) or a pharmaceutically acceptable salt thereof and a water-soluble solubilizer.

The specific examples of the definitions of compound (I) and the preferred working mode& of the invention are described in detail below.

The term "lower" as used in this specification means, unless otherwise indicated, any number of carbon atoms between 1 and 6, inclusive.

Suitable "alkyl" means straight or branched saturated aliphatic hydrocarbon residue and may include lower alkyl such as methyl, ethyl, propyl, isopropyl, butyl, isobutyl, pentyl, neopentyl, hexyl, and the like.

Suitable "alkenyl" means straight or branched unsaturated aliphatic hydrocarbon residue having one double bond and may include lower alkenyl such as vinyl, propenyl, butenyl, methylpropenyl, pentenyl, hexenyl, and the like.

Suitable "aryl" may include phenyl, tolyl, xylyl, cumenyl, mesityl, naphthyl, and the like.

Suitable examples of the protective group in the "protected hydroxyl group" may include: 1-(lower alkylthio)(lower)alkyl groups such as lower alkylthiomethyl groups (e.g. methylthiomethyl, ethylthiomethyl, propylthiomethyl, isopropylthiomethyl, butylthiomethyl, isobutylthiomethyl, hexylthiomethyl, etc.), more desirably $C_1$–$C_4$ alkylthioethyl groups, and most desirably methylthiomethyl; tri-substituted silyl groups such as tri(lower)alkylsilyl groups (e.g. trimethylsilyl, triethylsilyl, tributylsilyl, tert-butyldimethylsilyl, tri-tert-butylsilyl, etc.); lower alkyl-diarylsilyl groups (e.g. methyldiphenylsilyl, ethyldiphenylsilyl, propyldiphenylsilyl, tert-butyldiphenylsilyl, etc.), more desirably tri($C_1$–$C_4$)alkylsilyl and $C_1$–$C_4$ alkyldiphenylsilyl groups and most desirably tert-butyldimethylsilyl and tert-butyldiphenylsilyl; and acyl groups such as aliphatic acyl groups, aromatic acyl groups and aliphatic acyl groups substituted by aromatic groups, which are derived from carboxylic acids, sulfonic acids or carbamic acids.

The aliphatic acyl group may includes lower alkanoyl groups which may optionally have one or more suitable substituents such as carboxy (e.g. formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.), cyclo(lower)alkoxy(lower)alkanoyl groups which may optionally have one or more appropriate substituents such as lower alkyl (e.g. cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.), camphorsulfonyl, lower alkylcarbamoyl groups having one or more suitable substituents such as carboxy or protected carboxy, for example carboxy(lower)alkylcarbamoyl groups (e.g. carboxymethylcarbamoyl, carboxyethylcarbamoyl, carboxypropylcarbamoyl, carboxybutylcarbamoyl, carboxypentylcarbamoyl, carboxyhexylcarbamoyl, etc.), protected carboxy(lower)alkylcarbamoyl groups such as tri(lower)alkylsilyl(lower)alkoxycarbonyl(lower)alkylcarbamoyl groups (e.g. trimethylsilylmethoxycarbonylethylcarbamoyl, trimethylsilylethoxycarbonylpropyl carbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

The aromatic acyl group may include aroyl groups which may optionally have one or more suitable substituents such as nitro (e.g. benzoyl, toluoyl, xyloyl, naphthoyl, nitrobenzoyl, dinitrobenzoyl, nitronaphthoyl, etc), arenesulfonyl groups which may optionally have one or more suitable substituent(s) such as halogen (e.g. benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.), and so on.

The aromatic group-substituted aliphatic acyl group may include ar(lower)alkanoyl groups which may optionally have one or more suitable substituent(s) such as lower alkoxy and trihalo(lower)alkyl (e.g. phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.), and so on.

Among the above-mentioned acyl groups, the more desirable acyl groups are $C_1$–$C_4$ alkanoyl groups which may optionally be substituted by carboxy, cyclo($C_5$–$C_6$)alkyloxy($C_1$–$C_4$)alkanoyl groups having two ($C_1$–$C_4$)alkyl groups in the cycloalkyl moiety, camphorsulfonyl, carboxy($C_1$–$C_4$) alkylcarbamoyl groups, tri($C_1$–$C_4$)alkylsilyl($C_1$–$C_4$) alkoxycarbonyl($C_1$–$C_4$)alkylcarbamoyl groups, benzoyl which may have one or two nitro groups, halogen-substituted benzenesulfonyl groups, phenyl($C_1$–$C_4$)alkanoyl groups having $C_1$–$C_4$ alkoxy and trihalo($C_1$–$C_4$)alkyl groups. Of these groups, the most desirable are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Suitable "5- or 6-membered N-, S- or O-containing heterocyclic ring" may include pyrrolyl, tetrahydrofuryl, and the like.

The pharmaceutically acceptable salt of compound (I) is a nontoxic salt, which may be the corresponding salt with an inorganic or organic base such as alkali metal salts (e.g. sodium salt, potassium salt, etc.), alkaline earth metal salts (e.g. calcium salt, magnesium salt, etc.), ammonium salt and amine salts (e.g. triethylamine salt, N-benzyl-N-methylamine salt, etc.) and so on.

Referring to compound (I), there may exist conformers or one pair or more of stereoisomers such as optical and geometrical isomers due to the asymmetric carbon or the double bond. Such conformers and isomers also fall within the scope of the invention.

The water-soluble solubilizer is preferably a water-soluble compound which has both a solubilizing effect on tricyclo compound (I) and a thickening effect on the solution or has a promoting effect on the absorption of tricyclo compound (I).

The water-soluble solubilizer having a thickening effect prolongs the retention time in conjunctival sac and hence contributes to the intraocular penetration of the active compound. Preferred examples of this type of water-soluble solubilizer include water-soluble cellulose polymers (e.g. methylcellulose, ethylcellulose, carboxymethylcellulose sodium, hydroxyethylcellulose, hydroxypropylcellulose, hydroxypropylmethylcellulose, etc.), polyvinyl alcohol, polyvinylpyrrolidone, and the like. Among these solubilizers, water-soluble cellulose polymers are more preferable and hydroxypropylmethylcellulose is most preferable.

Preferred examples of water-soluble solubilizers having a promoting effect on the absorption of tricyclo compound (I) include water-soluble glycols and particularly low-molecular water-soluble glycols (such as ethylene glycol, diethylene glycol, triethylene glycol, propylene glycol, etc.). The most desirable solubilizer of this type is propylene glycol.

The water-soluble solubilizer having a thickening effect and that having an absorption-promoting effect may be used independently or in combination.

The concentration of tricyclo compound (I) in the aqueous liquid composition of the invention is not critical but can be selected according to, for example, the type of water-soluble solubilizer. However, it is preferably in the range of 0.001 to 1 weight % and more preferably in the range of 0.005 to 0.5 weight %.

The concentration of the water-soluble solubilizer in the composition of this invention depends on the type of water-soluble solubilizer but is generally 0.01 to 20 weight % and preferably 0.1 to 10 weight %.

Furthermore, depending on the process for preparing the object composition, the concentration of tricyclo compound (I) and/or the species or the concentration of the water-soluble solubilizer, the aqueous liquid composition of the invention may be a suspension. In case of such suspensions, the water-soluble solubilizer may play a role of dispersing agent. Such suspensions can be expected to have the benefits of sustained release and stability as eye drop.

If desired, there may be incorporated in the aqueous liquid composition of the invention various additives which are commonly used in liquid preparations and particularly in eye drops, such as an isotonicity (for example, sodium chloride etc.), a buffer (for example, boric acid, disodium hydrogenphosphate, sodium dihydrogenphosphate, etc.), a preservative (for example, benzalkonium chloride, benzethonium chloride, chlorobutanol, etc.), a thickener (for example, sugars such as lactose, mannitol, maltose, etc., hyaluronic acid or its salts such as sodium hyaluronate, potassium hyaluronate, mucopolysaccharides such as chondroitinsulfuric acid, sodium polyacrylate, carboxy vinyl polymer, cross-linked polyacrylate salts, etc.).

The aqueous liquid composition for external use of the present invention can be manufactured by a step of solubilizing tricyclo compound (I) with said water-soluble solubilizer or, as an alternative, dissolving tricyclo compound (I) in an organic solvent, which can dissolve the tricyclo compound(I), such as ethanol, adding said water-soluble solubilizer and removing the solvent, a step of adding additives such as isotonicity, buffer, preservative, thickener, etc. as required and in appropriate quantities, and a step of adding water (e.g. physiological saline, distilled water, etc.).

In case that the aqueous liquid composition of the present invention is a suspension, it can be manufactured by a step of adding the water-soluble solubilizer in water (e.g. physiological saline, distilled water, etc.) and if necessary, additives such as isotonicity, buffer, preservative, thickener, etc. in the resultant solution, and a step of adding the tricyclo compound (I) in the resultant solution. Suitable quantitative ratio of the water-soluble solubilizer and the tricyclo compound (I) by weight may be from 0.01:1 to 100:1, preferably 0.1:1 to 50:1, more preferably 0.5:1 to 5:1.

EFFECTS

The effects of the present invention are described below by the following.

TEST SAMPLES

Eye drop (1) . . . The eye drop prepared by Example 4

Control . . . An oily eye drop of FK506 (0.01%) (prepared by adding olive oil to FK506 and dissolving it with stirring)

TEST METHOD

Using male SD rats (body weights 275~405 g) aged 8~10 weeks, 10 $\mu$l portions of each test eye drops were instilled into both eyes five times at 5-minute intervals. After 1 hour, the rats were bled to death and both eyes were enucleated. The concentrations of FK506 in the cornea and lens of each isolated eye were determined by the conventional enzyme immunoassay method (for example, the indirect method described in Japanese Kokai Patent Publication No. 1-92659/1989).

The results are set forth in Tables 1 and 2. And the data are all expressed in mean ±SEM.

TEST RESULTS

TABLE 1

The concentration of FK506 in the cornea

| Test Samples | Concentration of FK506 (ng/g) After 1 hr |
|---|---|
| Eye drop (1) | 2218.8 ± 470.1 |
| Control | N.D.* |

* . . . Not detectable (detection limit: 20 ng/g)

TABLE 2

The concentration of FK506 in the crystalline lens

| Test Samples | Concentration of FK506 (ng/g) After 1 hr |
|---|---|
| Eye drop (1) | 2.8 ± 0.7 |
| Control | N.D.* |

* . . . Not detectable (detection limit: 6 ng/g)

It is apparent from the above results that the aqueous liquid composition of the present invention not only has the desirable characteristics of an aqueous preparation for external use but a high efficiency of penetration into bodies, particularly into ocular tissues. Therefore, the aqueous liquid composition of the present invention is particularly useful for the treatment and prevention of various diseases of the eye such as autoimmune diseases and so on (e.g. vernal conjunctivitis, uveitis associated with Behcet's disease, keratitis, herpetic keratitis, conical cornea, dystrophia epithelialis corneae, leukoma, ocular pemphigus, Mooren's ulcer, Sclevitis, Graves' ophthalmopathy, etc.) and rejection to corneal transplantation.

While the above-mentioned dosage of the aqueous liquid composition varies with the patient's age and condition, the effective dose can be chosen for each condition or case.

The following examples are further illustrative of the invention.

EXAMPLE 1

In 100 ml of the composition

| | |
|---|---|
| FK506 | 0.01 g |
| Hydroxypropylmethylcellulose 2906 | 1.00 g |
| Physiological saline | q.s. |

FK506 is dissolved in an appropriate amount of ethanol and, then, hydroxypropylmethylcellulose 2906 is added. After stirring, the ethanol is removed under reduced pressure and the residue is diluted with sufficient physiological saline to make 100 ml. The mixture is stirred to dissolve the solid to give an eye drop.

EXAMPLE 2

In 100 ml of the composition

| | |
|---|---|
| FK506 | 0.01 g |
| Propylene glycol | 5.00 ml |
| Physiological saline | q.s. |

In propylene glycol is dissolved FK506 with stirring and the solution is diluted with sufficient physiological saline to make 100 ml. The mixture is stirred to give an eye drop.

EXAMPLE 3

In 100 ml of the composition

| | |
|---|---|
| FK506 | 0.01 g |
| Hydroxypropylmethylcellulose 2906 | 1.00 g |
| Propylene glycol | 5.00 ml |
| Physiological saline | q.s. |

FK506 is dissolved in an appropriate amount of ethanol, followed by addition of hydroxypropylmethylcellulose 2906. After stirring, the ethanol is removed under reduced pressure and the residue is diluted with propylene glycol and sufficient physiological saline to make 100 ml. The mixture is stirred well to give an eye drop.

EXAMPLE 4

In 100 ml of the composition

| | |
|---|---|
| FK506 | 100 mg |
| Hydroxypropylmethylcellulose 2906 | 350 mg |
| Disodium hydrogenphosphate | 18.4 mg |
| Sodium dihydrogenphosphate | 1547 mg |
| Phosphoric acid | 0.32 mg |
| Sodium chloride | 288 mg |
| Benzalkonium chloride | 20 mg |
| Distilled water | q.s. |

Phosphate buffer (pH 4.5, 100 ml) is prepared by using disodium hydrogenphosphate, sodium dihydrogenphosphate, phosphoric acid and distilled water. After dissolving sodium chloride, benzalkonium chloride and hydroxypropylmethylcellulose 2906 in the said phosphate buffer (95 ml), FK506 is added in the resultant solution.

After stirring sufficiently, the resultant suspension is diluted with the suitable amount of phosphate buffer to make 100 ml. The suspension is stirred well to give an aqueous suspending eye drop.

EXAMPLE 5

In 100 ml of the composition

| | |
|---|---|
| FK506 | 100 mg |
| Methylcellulose | 10 mg |
| Disodium hydrogenphosphate | 18.4 mg |
| Sodium dihydrogenphosphate | 1547 mg |
| Phosphate | 0.32 mg |
| Sodium chloride | 288 mg |
| Benzalkonium chloride | 20 mg |
| Distilled water | q.s. |

An aqueous suspending eye drop is prepared according to a similar manner to that of Example 4.

EXAMPLE 6

In 100 ml of the composition

| | |
|---|---|
| FK506 | 100 mg |
| Polyvinyl alcohol | 1400 mg |
| Disodium hydrogenphosphate | 18.4 mg |
| Sodium dihydrogenphosphate | 1547 mg |
| Phosphate | 0.32 mg |
| Sodium chloride | 288 mg |
| Benzalkonium chloride | 20 mg |
| Distilled water | q.s. |

An aqueous suspending eye drop is prepared according to a similar manner to that of Example 4.

What we claim is:

1. An aqueous liquid eye drop suspension composition comprising a tricyclo compound of the formula:

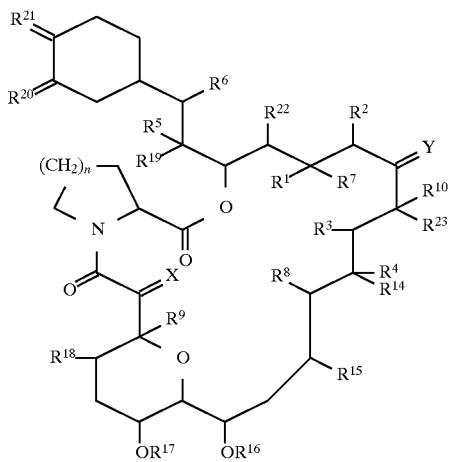

I wherein each vicinal pair of substituents [$R^1$ and $R^2$], [$R^3$ and $R^4$], [$R^5$ and $R^6$] independently a) represent two vicinal hydrogen atoms, or b) form a second bond between the vicinal carbon atoms to which they are attached; in addition to its significance above, $R^2$ may represent an alkyl group;

$R^7$ represents H, OH, protected hydroxy or O-alkyl, or in conjunction with $R^1$ it may represent =0;

$R^8$ and $R^9$ independently represent H or OH;

$R^{10}$ represents H, alkyl, alkyl substituted by one or more hydroxyl groups, alkenyl, alkenyl substituted by one or more hydroxyl groups, or alkyl substituted by =O;

X represents O, (H,OH), (H,H) or —CH$_2$O—;

Y represents O, (H, OH), (H,H,), N—NR$^{11}$R$^{12}$ or N—OR$^{13}$;

$R^{11}$ and $R^{12}$ independently represent H, alkyl, aryl or tosyl;

$R^{13}$, $R^{14}$, $R^{15}$, $R^{16}$, $R^{17}$, $R^{18}$, $R^{19}$, $R^{22}$ and $R^{23}$ independently represent H or alkyl;

$R^{20}$ and $R^{21}$ independently represent O, or they may independently represent ($R^{20}$a,H) and ($R^{21}$a,H) respectively; $R^{20}$a and $R^{21}$a independently represent OH, O-alkyl or OCH$_2$OCH$_2$CH$_2$OCH$_3$ or $R^{21}$a is protected hydroxy;

in additional, $R^{20}$a and $R^{21}$a may together represent an oxygen atom in an epoxide ring;

n is 1, 2 or 3;

or a pharmaceutically acceptable salt thereof; polyvinyl alcohol; and a balance water, wherein said compound and polyvinyl alcohol are present in a ratio of 1:0.01 to 1:100 by weight.

2. The aqueous liquid eye drops suspension composition of claim 1, wherein the tricyclo compound (I) and polyvinyl alcohol are present in a ratio of 1:0.1 to 1:50 by weight.

3. The aqueous liquid eye drop suspension composition of claim 2, wherein the tricyclo compound (I) is represented by the formula shown below:

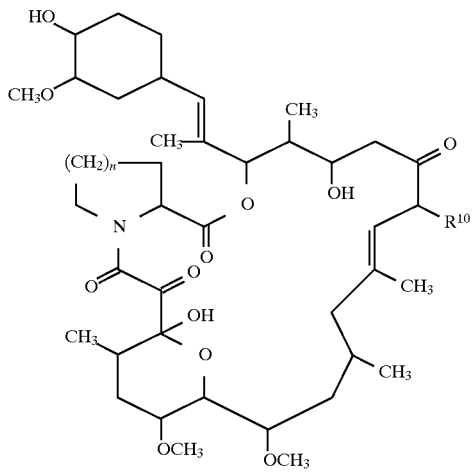

wherein $R^{10}$ is methyl, ethyl, propyl or allyl, and n is an integer of 1 or 2, provided that when n is 1, then $R^{10}$ is allyl.

4. The aqueous liquid eye drop suspension composition of claim 3, wherein the tricyclo compound is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

5. The aqueous liquid eye drop suspension composition of claim 1, which comprises, as an additional element, at least one of an isotonicity agent, a buffer, a preservative and a thickener.

* * * * *